United States Patent [19]

Pitha et al.

[11] Patent Number: 5,120,720
[45] Date of Patent: Jun. 9, 1992

[54] PREPARATION OF LIPOPHILE:HYDROXYPROPYLCYCLODEXTRIN COMPLEXES BY A METHOD USING CO-SOLUBILIZERS

[75] Inventors: Josef Pitha, Baltimore, Md.; Juan J. Torres-Labandeira, Coruna, Spain; Tetsumi Irie, Kumamoto, Japan

[73] Assignee: The United States of America as represented by the Secretary of the Department of Health & Human Services, Washington, D.C.

[21] Appl. No.: 585,792

[22] Filed: Sep. 20, 1990

[51] Int. Cl.$^5$ .................. A61K 9/18; C08B 37/16
[52] U.S. Cl. ........................ 514/58; 536/103
[58] Field of Search ............ 514/58; 536/103

[56] References Cited

U.S. PATENT DOCUMENTS

| | | | |
|---|---|---|---|
| 4,727,064 | 2/1988 | Pitha | 514/58 |
| 4,877,774 | 10/1989 | Pitha et al. | 514/58 |
| 4,877,778 | 10/1989 | Carpenter et al. | 514/58 |
| 5,024,997 | 6/1991 | Motola et al. | 514/58 |

FOREIGN PATENT DOCUMENTS

WO85/02767 7/1985 PCT Int'l Appl.
WO9003784 4/1990 PCT Int'l Appl.

OTHER PUBLICATIONS

Anaissie et al., U.S. patent application SN 07/345,928.
Kurozumi et al., Chem. Pharm. Bull., 23 (12) pp. 3062-3068 (1975).
Vikmon, M. et al., J. Antibiot., vol. 38, pp. 1822-1824 (1985).
Pitha et al., Internatl. Journ. of Pharmaceutics, vol. 29, pp. 73-82 (1986).
Torres-Labandeira et al., J. Pharm. Sci., vol. 80, No. 4, pp. 384-386 (Apr. 1990).
Kajtar et al., Biopolymers, vol. 28, pp. 1585-1596 (1989).
W. Hirsch et al., Can. J. Chem., vol. 65, pp. 2661-2664 (1987).
R. I. Gelb et al., J. Am. Chem. Soc., vol. 104, pp. 6283-6288 (1982).
T. Cserhati et al., Journal of Chromatography, vol. 259, pp. 107-110 (1983).

*Primary Examiner*—Ronald W. Griffin
*Attorney, Agent, or Firm*—Birch, Stewart, Kolasch & Birch

[57] ABSTRACT

The dissolution of lipophilic compounds in aqueous solutions of hydroxypropylcyclodextrins can be accelerated by the addition of co-solubilizers, such as ethanol or ammonia, which again can be removed, together with water, by evaporation or by freeze-drying leaving lipophile: hydroxypropylcyclodextrin complexes as a residue. The co-solubilizer method was used successfully with steroid drugs (5-androstene-3$\beta$,17$\beta$-diol, 4-androstene-3,17-dione, dehydroepiandrosterone, dexamethasone, 5-$\alpha$-dihydro-testosterone, 6-methylprednisolone, and testosterone), peptides (gramicidin S) and a macrocyclic antibiotic (amphotericin B). The complexes prepared in this manner were amorphous and possessed satisfactory stability.

19 Claims, No Drawings

PREPARATION OF LIPOPHILE:HYDROXYPROPYLCYCLODEXTRIN COMPLEXES BY A METHOD USING CO-SOLUBILIZERS

FIELD OF THE INVENTION

The present invention relates to inclusion complexes between lipophilic compounds and hydroxypropylcyclodextrin complexes and to methods for preparing such utilizing co-solubilizers.

BACKGROUND OF THE INVENTION

The solubility in water of many lipophilic compounds may be increased through the formation of inclusion complexes with cyclodextrins and their derivatives. Szejtli in *Cyclodextrin Technology* (pp. 186–306) gives many examples of the uses of such solubilization in pharmaceuticals. In a majority of the described pharmaceutical applications underivatized cyclodextrins, which are crystalline, or crystalline derivatives thereof are utilized to increase the water solubility of lipophilic compounds. However, improvements in solubility could also be obtained when amorphous derivatives of cyclodextrins were used instead of crystalline derivatives (e.g., hydroxypropylcyclodextrins). (J. Pitha, U.S. Pat. No. 4,727,064; B. W. Müller, U.S. Pat. No. 4,764,604).

Complexes of cyclodextrins and their crystalline derivatives with lipophiles have often been prepared by co-dissolution of components in water (Szejtli, 1.c., pp. 80–90). In some instances (e.g., vitamin $D_3$, Szejtli, 1.c., pp. 85 and 268) addition of an organic solvent (ethanol, acetone) was necessary, but such solvents could be used only sparingly since they precipitated the cyclodextrins utilized. Today, when such cyclodextrin complexes are prepared on a technical scale, a solid phase method of preparation (kneading of components) is the method of choice.

Improvements in the pharmaceutical usefulness of peptides by using hydroxypropylcyclodextrin was studied by Hora et al. The studied peptides included several hormones and peptidic factors; no co-solvent was used in the study (Hora et al, Int. Applic. No. PCT US 89 04099).

The preparation of the amorphous hydroxypropylcyclodextrin complexes has usually required prolonged stirring of components in water (J. Pitha, U.S. Pat. No. 4,727,064 and B. W. Müller, U.S. Pat. No. 4,764,604). In contrast to cyclodextrins, hydroxypropylcyclodextrins are quite soluble in polar organic solvents, including 190 proof U.S. Pharmacopeia ethanol (J. Pitha et al., *Int. J. Pharm.* 29, 73–82, 1986). Nevertheless, the addition of organic solvents at such solubilizing concentrations has not been used in the preparation of such complexes, since there has been the additional concern that nearly all solvents form complexes with cyclodextrins, and thus solvent molecules may displace the solubilized lipophile from formed inclusion complexes. In this regard, Table 1 contains data on reported stability constants of complexes of solvents with α- and β-cyclodextrin.

Ammonia has previously been used as a co-solubilizer in the preparation of complexes of crystalline cyclodextrins with non-steroidal antiinflammatory drugs (K. Kurozumi et al., *Chem. Pharm. Bull.* 23, 3062–3068, 1975). Ammonia was also used as a co-solubilizer in the preparation of pancratistatin:hydroxypropyl-β-cyclodextrin complex (J. Torres-Labandeira, P. Davignon, and J. Pitha, *J. Pharm. Sci.*, accepted for publication, June 1990). Ammonia forms a quite stable complex with cyclodextrins (Table 1).

Concerning macrocyclic antibiotics, the first example studied was polymyxin, which was found to form complexes with β-cyclodextrin derivatives (Cserkali et al., *J. Chromatoor.* 259, 107–110, 1983). Another antibiotic of this type, amphotericin B, was the subject of U.S. Pat. No. 4,883,785 of Chow et al.; these inventors disclosed that amphotericin B can be solubilized by the addition of the drug to an alkaline solution of cyclodextrins, preferably γ, followed by neutralization of the solution. Complexes of amphotericin B with underivatized cyclodextrins were also the subject of a publication by Vikmon et al. (*J. Antibiot.* 38, 1822–1824, 1985) and by Rajagopalan et al. (*Int. J. Pharm.* 29, 161–168, 1986). U.S. patent application, Ser. No. 07/345,928 by Anaissie et al. addressed the solubilization of amphotericin B and other macrocyclic antibiotics by hydroxypropylcyclodextrins, but no cosolvent was used in the preparations described there.

TABLE 1

| Stability constants ($M^{-1}$) of the complexes of solvents with α- and β-cyclodextrin | | | | |
|---|---|---|---|---|
| Solvent | α-cyclodextrin | | β-cyclodextrin | |
| methanol |  | 1(b) | 1(a) |  |
| ethanol | 5(a) | 6(b) 4.8(c) | 1(a) | 1(b) |
| n-propanol | 20(a) | 23(b) | 5(a) | 4(b) |
| 2-propanol | 3(a) | 5(b) 4.6(c) | 2(a) | 4(b) |
| n-butanol | 110(a) | 89(b) | 15(a) | 17(b) |
| t-butanol | 2(a) | 4(b) 4.1(c) | 42(a) | 48(b) |
| n-pentanol | 300(a) | 323(b) | 87(a) | 63(b) |
| 2,2-dimethyl-1-propanol | 30(a) |  | 660(a) | 580(b) |
| ammonia | 61000(d) |  | 15000(d) |  |
| dimethyl sulfoxide | 0.4(c) |  |  |  |
| dioxane | 4.4(c) |  |  |  |

(a)taken from M. Suzuki et al., Chem. Pharm. Bull. 36, 720–725, 1988;
(b)taken from Y. Matsui and K. Mochida, Bull. Chem. Soc. Japan 52, 2808–2814, 1979.
(c)taken from R. I. Gelb et al., J. Am. Chem. Soc. 104, 6283–6288, 1982;
(d)taken from W. Hirsch et al., Can. J. Chem. 65, 2661–2664, 1987.

SUMMARY OF THE INVENTION

One object of the present invention is to provide complexes of lipophilic compounds which possess improved water solubility, as compared with the free lipophilic compound. Another object of the present invention is to provide a method of preparing such complexes which is not overly time consuming for those skilled in the art, and which can in turn be utilized in large scale manufacturing processes, with little, if any, difficulty. Still another object is to provide complexes with lipophilic compounds which complexes are physically stable and which can advantageously be utilized in pharmaceutical compositions for the treatment of diverse physical conditions.

The above objects are accomplished in the present invention with the provision of amorphous lipophilic hydroxypropylcyclodextrin complexes, and processes for their preparation, which comprises the steps of dissolving a lipophilic component and a hydroxypropylcyclodextrin component in an aqueous solution containing a volatile co-solvent, and then evaporating or lyophilizing the solution to provide the desired amorphous complex. Pharmaceutical compositions which contain the amorphous complexes and as pharmaceutically acceptable carrier are also provided.

DETAILED DESCRIPTION OF THE PREFERRED EMBODIMENTS

The following detailed description is provided in order to aid those skilled in the art in practicing the present invention. Even so, the following discussions and Examples should not be deemed to unduly limit the present invention, since modifications may easily be made in the procedures herein taught by those of ordinary skill in the art, without departing from the spirit or scope of the present invention. In this regard, the present invention is only to be limited by the scope of the claims appended hereto and the equivalents thereof.

The following glossary of terms is intended to define the meaning of certain words as used herein.

The term "amorphous" is an adjective as used herein, which means "consisting essentially without crystalline phases".

The term "lipophile" as used herein, means a compound which possesses an affinity for fat and which can form an amorphous inclusion complex with a hydroxypropylcyclodextrin, as herein taught. Such lipophile compounds can include steroids, proteins, vitamins, and the like.

The term "Vitamin D" as used herein, includes any of several fat soluble molecules of natural or synthetic origin, that are converted by animals into metabolites that control calcium and phosphorous homeostasis in a hormonal like manner. Included within the group are Vitamin $D_2$ and $D_3$, among others.

The term "Vitamin E" as used herein, is a generic description for all tocol and tocotrienol derivatives having qualitatively the biological activity of $\alpha$-tocoperol.

The term "volatile co-solvent" as used herein, means a solvent (other than water) which will evaporate at room temperature and standard pressure, and which is water miscible. Preferably, the co-solvent is a better solubilizer of the lipophile than water, and is present the particular co-solvent utilized and the lipophile being dissolved. Exemplary of suitable co-solvents are ammonium, ethyl alcohol and the like.

When preparing complexes of lipophiles with hydroxypropylcyclodextrins, the addition of evaporative solvents such as ethanol and ammonia as co-solubilizers makes the production of such complexes faster and more convenient than when water is used solely in the dissolution step. Moreover, since hydroxypropylcyclodextrins dissolve well in ethanol, USP ethyl alcohol (190 proof) can be used as a co-solubilizer, if desired. In the present disclosure, steroids and peptides are used to illustrate the process of the present invention by which lipophile:hydroxypropylcyclodextrin compounds may be formed. However, the same is not limiting to the present invention since many different lipophilic compounds (e.g., vitamins D and E) can also form complexes with hydroxypropylcyclodextrin using the processes disclosed herein. Nonetheless, exemplary of steroids with which complexes may be formed, and which are provided herein as Examples, are 5-androstene-3$\beta$,17$\beta$-diol, 4-androstene-3,17-dione, dehydroepiandrosterone, dexamethasone, 5-$\alpha$-dihydrotestosterone, 6-methylprednisolone, and testosterone (Examples 1-3).

In the following experimental section, steroids were dissolved in ethanol together with ten times their weight of hydroxypropyl-$\beta$-cyclodextrin, and solutions evaporated leaving residues of a glassy appearance. These residues could easily be screened visually for crystalline phase.

No crystalline phases were observed in any of the complexes provided in Examples below, but with some others, e.g., thalidomide, crystals were visible and the formation of an amorphous complex therewith was incomplete. For additional confirmation of the absence of crystalline phases x-ray powder diffraction and differential scanning calorimetry data were obtained for the combination of testosterone with hydroxypropyl-$\beta$-cyclodextrin (Example 3).

For a number of applications, complexes in powdery form as prepared by freeze-drying (lyophilizing), are preferable to the glassy residues such as are obtained by the above discussed procedure. Therefore, to obtain complexes in a powdery form, the glassy preparations were dissolved in water (final concentration of hydroxypropyl-$\beta$-cyclodextrin was about 10% W/W), sterilized by ultrafiltration and freeze-dried. All of the following exemplary preparations of steroids so prepared, dissolved fully. Moreover, the complexes so obtained were again amorphous and could be tabletted by direct compression.

The solubility of freeze-dried complexes such as those provided below was invariably high. For example, all the complexes of steroids in Examples 1-3 dissolved smoothly in water up to 40% W/W concentration, and these solutions were stable for at least 24 hours.

The stabilitY of the amorphous states of the oomplex was also studied. For example, X-ray powder diffraction patterns of the testosterone:hYdroxypropyl-$\beta$-cyclodextrin preparation (Example 3) was measured after one and four weeks of storage at ambient temperature and humidity. The pattern remained amorphous, with the only observable change being a slight shift with differences at the low end of the diffraction patterns. Such changes are thought to be probably caused by changes in shape and size of particles in the complexes.

The methods of preparation herein disclosed were also used successfully with the ethanol-soluble peptides such as gramicidin S, complexed with hydroxypropyl-$\beta$-cyclodextrin (Example 4). It was also used to prepare the gramicidin S:hydroxypropyl-$\alpha$-cyclodextrin preparation (Example 5) and gramicidin S:hydroxypropyl-$\gamma$-cyclodextrin preparation (Example 6). Nevertheless, we note the method failed with gramicidin D. In that instance, the peptide gramicidin D did not dissolve in ethanol 75% and even though it dissolved in ethanol 95%, after evaporation of the solution, the resulting solid residue was insoluble in water.

The processes disclosed herein differ substantially from those described by Szejtli (p. 268) for the preparation of crystalline $\beta$-cyclodextrin:vitamin $D_3$ complexes, which were prepared using organic solvents. In this regard, the procedure described by Szejtli consists of the co-dissolution of components, i.e., of crystalline $\beta$-cyclodextrin and vitamin $D_3$, at 50° C. in 60-65% aqueous ethanol, followed by cooling of the clear solution during which crystalline complex of the vitamin precipitates. Moreover, attempts to use Szejtli's procedure for the above complexes were not successful, since concentration of ethanol in the range 60-65% solubilized steroids only incompletely and no precipitation occurred. The same time the conditions disclosed here were not suitable for the preparation of 5 Szejtli's complex (i.e., β-cyclodextrin:vitamin D₃) since β-cyclodextrin had twoo low solubility (less g/L in 75% ethanol) for the process to be practical.

Use of aqueous ammonia as a co-solubilizer is illustrated on the preparation of amphotericin B:hydroxypropyl-β-cyclodextrin complex (Example 7). low solubility and is prone to hydrolysis. Solutions of ammonia (Range 7.4-18.5%) were used to dissolve the drug, then hydroxypropyl-β-cyclodextrin, in aqueous solution was added, and solution immediately freeze-dried. The same process was successful with hydroxypropyl-γ-cyclodextrin as well. The powder remaining after freeze-drying was amorphous when examined by x-ray diffraction, and did not contain any ammonia detectable by Nessler reagent. The stability of the drug in the complex was re-checked by thin layer chromatography; four weeks of storage at room temperature did not lead to any detectable decomposition.

Solubility of the amphotericin B complexes and the stability of its solutions was found to depend on the ratio of drug to hydroxypropylcyclodextrin. Both of these parameters increased when excess of hydroxypropylcyclodextrin was used (Table 2). Comparison of the results on complexes of amphotericin B with hydroxypropyl-β- or γ-cyclodextrins prepared by the ammonia method showed that the latter yielded solutions which were slightly more stable (Table 2).

Absorption spectra of amphotericin B are strongly solvent-dependent (M. Kajtar et al, *Biopolymers* 28, 1585-1589, 1989). Spectra of amphotericin B:hydroxypropyl-β-cyclodextrin were of the type seen when drug was solubilized by deoxycholate, i.e., in micellar solutions. Spectra of amphotericin B:hydroxypropyl-γ-cyclodextrin complexes at high excesses of solubilizer were clearly of the type found in organic solvent, i.e., when there is no association between drug molecules (M. Kajtar et al, *Biopolymers* 28, 1585-1589, 1989). When amount of the host compound was decreased, the spectra was of the intermediate type.

The above process for amphotericin B solubilization differs substantially from that described in U.S. Pat. No. 4,883,785. There, in Example 3, is described the solubilization of amphotericin B by β-cyclodextrin in aqueous sodium hydroxide and subsequent neutralization of the solution with phosphoric acid. Only about 1% of the starting drug was solubilized by that procedure, compared to the nearly complete solubilization obtained here. The process described in U.S. Pat. No. 4,883,785 obviously lacks in two aspects compared to the process presented here. Firstly, crystalline cyclodextrins, which are much less water soluble than hydroxypropylcyclodextrins were employed. Secondly, the use of sodium hydroxide to solubilize amphotericin B and of phosphoric acid to neutralize the alkaline solution of amphotericin B and β-cyclodextrin is not optimal. Sodium hydroxide, in difference to ammonia is not . volatile; furthermore, phosphoric acid is known to form complexes with β-cyclodextrin (J. Szejtli et al, Belg. Pat. 890759) what furthermore complicates the preparation. It should also be noted that the improvement here disclosed, i.e., use of ammonia instead of sodium hydroxide, cannot be assumed to be possible without experimental proof. β-Cyclodextrin forms very stable complexes with ammonia (W. Hirsch et al, *Can. J. Chem.* 65, 2661-2664, 1987) and thus, the final product could well have been uncomplexed amphotericin B mixed with ammonia:hydroxypropylcyclodextrin complex.

EXPERIMENTS

EXAMPLE 1

Preparation of steroid:hydroxypropyl-β-cyclodextrin complex using 75% ethanol.

Dehydroepiandrosterone (2.5 g) and hydroxypropyl-β-cyclodextrin (25 g, average degree of substitution 5.4 per molecule) were dissolved in 75% V/V ethanol (200 mL). Full dissolution occurred in five minutes; the solution was then filtered through a membrane filter (pore size 0.22 μm). The filtrate was evaporated at room temperature in vacuo to dryness leaving a glassy residue. That was dissolved in distilled water (200 mL), the clear solution sterilized by filtration through a membrane filter (pore size 0.45 μm), and freeze-dried to give a powdery complex. The yield was 85%. The solubility of the complex in distilled water was over 40% W/W.

The above procedure was also applied to 4-androstene-3,17-dione and testosterone; the yields were 87 and 91%, respectively. The solubility in water was in both cases at least 40% W/W.

EXAMPLE 2

Preparation of steroid:hydroxypropyl-β-cyclodextrin complex using 95% ethanol (190 proof).

5-Androstene-3β,17β-diol (0.5 g) and hydroxypropyl-β-cyclodextrin (5 g) were dissolved in 190 proof ethanol (50 mL). As soon as dissolution occurred (5 min), the solution was filtered through a membrane filter (pore size 0.22 μm). The filtrate was evaporated at room temperature in vacuo to dryness. The residue dissolved clearly in distilled water (50 mL). This solution was filtered through a membrane filter (pore size 0.45 μm) and freeze-dried, yielding a powdery complex. The yield was 90%. The solubility of the complex in distilled water was over 40% W/W.

The above procedure was also applied to 5-α-dihydrotestosterone, dexametasone, 6-α-methylprednisolone and testosterone. The yields were 91, 93, 95, and 89%, respectively. The solubility all the complexes in water was at least 40% W/W.

EXAMPLE 3

Preparation of the steroid:hydroxypropyl-β-cyclodextrin complex using 190 proof ethanol and evaporation at atmospheric pressure.

Testosterone (1 g) and hydroxypropyl-β-cyclodextrin (10 g) were dissolved in 190 proof ethanol (100 mL). As soon as dissolution occurred (5 min), the solution was filtered through a membrane filter (pore size 0.22 μm). The filtrate was evaporated by immersing of the flask with the solution into a water bath and by blowing a stream of argon through the solution. The residue was dissolved in distilled water (100 mL). This solution was filtered through a membrane filter (pore size 0.45 μm) and freeze-dried, yielding a powdery complex. The yield was 85%. The solubility of the complex in water was at least 40% W/W.

EXAMPLE 4

Preparation of peptide:hydroxypropyl-β-cyclodextrin complex.

Gramicidin S (0.5 g) and hydroxypropyl-β-cyclodextrin (5 g) were dissolved in 190 proof ethanol (50 mL). As soon as dissolution occurred (5 min), the solution was filtered through a membrane filter (pore size 0.22

μm). The filtrate was evaporated in vacuo to dryness. The residue dissolved clearly in distilled water (50 mL). This solution was filtered through a membrane filter (pore size 0.45 μm) and freeze-dried to a powdery complex. The yield was 87%. The solubility of the complex in water was at least 40% W/W.

EXAMPLE 5

Preparation of peptide:hydroxypropyl-α-cyclodextrin complex.

Gramicidin S (0.06 g) and hydroxypropyl-α-cyclodextrin (0.6 g, average degree of substitution 4.6 per molecule) were dissolved in 190 proof ethanol (10 mL). As soon as dissolution occurred (5 min), the solution was filtered through a membrane filter (pore size 0.22 μm). The filtrate was evaporated in vacuo to dryness. The residue dissolved clearly in distilled water (10 mL). This solution was filtered through a membrane filter (pore size 0.45 μm) and freeze-dried to a powdery complex. The yield was 85%. The solubility of the complex in water was at least 40% W/W.

EXAMPLE 6

Preparation of peptide:hydroxypropyl-γ-cyclodextrin complex.

Gramicidin S (0.05 g) and hydroxypropyl-γ-cyclodextrin (0.05 g, average degree of substitution 5.6 per molecule) were dissolved in 190 proof ethanol (10 mL). As soon as dissolution occurred (5 min), the solution was filtered through a membrane filter (pore size 0.22 μm). The filtrate was evaporated in vacuo to dryness. The residue dissolved clearly in distilled water (10 mL). This solution was filtered through a membrane filter (pore size 0.45 μm) and freeze-dried to yield a powdery complex.

EXAMPLE 7

Preparation of macrocyclic lactone:hydroxypropyl-β-cyclodextrin complex using ammonia.

Amphotericin B (0.2 g) was dissolved in 15 mL ammonia hydroxide:water (1:2, about 12% ammonia) solution. The dissolution, when accelerated by sonication, occurred within 5 min. Immediately after the dissolution, the aqueous solution hydroxypropyl-β-cyclodextrin (3 mL; concentration, 6.25% W/W; 1:10 W/W drug:cyclodextrin derivative) was added. The solution was then promptly filtered through a membrane filter (pore size 0.45 μm), and the filtrate immediately freeze-dried. The yield of the process was 87%. The solubility of the complex in water and stability of the solutions are given in Table 2.

The amorphous lipophile:hydroxypropylcyclodextrin inclusion complexes of the present invention may be made into sterile pharmaceutical compositions for injection, by combination with appropriate pharmaceutically acceptable carriers or diluents, or they may be formulated into solid or liquid preparations for oral administration in the usual ways for such a respective route of administration. Thus, the following methods and excipients are merely exemplary and are in no way to be construed as limiting.

In pharmaceutical dosage forms, the amorphous inclusion complexes of the present invention may be used alone or in appropriate association, as well as in combination with other pharmaceutically active compounds, if desired.

The amorphous inclusion complexes may be formulated into preparations for injection by dissolving, suspending or emulsifying them in an aqueous solvent, and if desired, with conventional additives such as isotonic agents, stabilizers, preservatives or the like.

The amount of the compounds of the amorphous inclusion complexes to be administered will, of course, vary according to lipophile present and the condition treated. When treating a specific condition, a suitable and preferred dosage is that amount sufficient to render controllable the specific condition encountered.

The amorphous inclusion complexes provided for herein may be formulated into unit dosage forms, wherein the term "unit dosage forms" refers to physically discrete units suitable as unitary dosages for human as well as animal subjects, each unit containing a predetermined quantity of an amorphous inclusion complex herein disclosed, calculated in an amount sufficient with a pharmaceutically acceptable, diluent, carrier or vehicle. Specifications for the novel unit dosage forms of the present invention depend on the particular complex employed and the effect to be achieved, and the pharmacodynamics associated with each lipophile complex in the host treated.

The pharmaceutically acceptable adjuvants useful herein (for example, vehicles, carriers and diluents), are readily known and available to those skilled in the art.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

REFERENCE CITED

U.S. PATENT DOCUMENTS

1. Anaissie, E., Bodey, G., and Pitha, J., U.S. patent application, Ser. No. 07/345,928.

Pharmaceutical Compositions

TABLE 2

Amphotericin B:hydroxypropylcyclodextrin complexes prepared with ammonia as co-solubilzer: solubility and stability in solution

| Compound | Ratio of drug to hydroxypropyl-cyclodextrin W/W | Concentration of the complex (% W/W) | | |
|---|---|---|---|---|
| | | 3% | 10% | 40% |
| hydroxypropyl-β-cyclodextrin | 1:10 | clear up to 48 h | clear up to 1 h | not dissolved |
| | 1:100 | clear up to 48 h | clear up to 48 h | clear up to 15 min |
| | 1:200 | clear up to 48 h | clear up to 48 h | clear up to 15 min |
| | 1:400 | clear up to 48 h | clear up to 48 h | clear up to 2 h |
| hydroxypropyl-γ-cyclodextrin | 1:10 | clear up to 48 h | clear up to 15 min | not dissolved |
| | 1:100 | clear up to 48 h | clear up to 48 h | clear up to 48 h |
| | 1:200 | clear up to 48 h | clear up to 48 h | clear up to 48 h |

2. Chow, W. S., Chen, S. C., and Timmins, P., Complex U.S. Pat. No. 4,883,785, 1989.
3. Müller, B. W., U.S. Pat. No. 4,764,604
4. Pitha, J., Pharmaceutical Preparations Containing Cyclodextrin Derivatives, U.S. Pat. No. 4,727,064, 1988.

FOREIGN PATENT DOCUMENTS

1. Szejtli, J., Budai, Zs., Dencs, A., and Kerekes, A., Belg. Pat. 890759.
2. Hora, M. S., Rubenfeld, J., Stern, W. and Wang, G. J. Cyclodextrin-Peptide Complexes, International Publication Number WO 90103784, International Applic. Number PCT US 89 04099.

OTHER PUBLICATIONS

1. Cserhali et al., *J. Chromatogr.* 259, 107–110, 1983.
2. Gelb, R. I., Schwartz, L. M., Radeos, M., Edmonds, R. B., and Laufer, D. A., *J. Am. Chem. Soc.* 104, 6283–6288, 1982.
3. Hirsch, W., DiMartini, C., and Fried, V., *Can. J. Chem.* 65, 2661–2664, 1987.
4. Kajtar, M., Vikmon, M., Morlin, E., and Szejtli, J., *Biopolymers* 28, 1585–1589, 1989.
5. Kurozumi, K., Nambu, N., and Nagai, T., *Chem. Pharm. Bull.* 23, 3062–3068, 1975.
6 Matsui, Y., and Mochida, K., *Bull. Chem. Soc. Japan* 52, 2808–2814, 1979.
7. Pitha, J., Milecki, J., Fales, H., Pannell, L., and Uekama, K., *Int. J. Pharm.* 29, 73–82, 1986.
8. Rajagopalan, N., Chen, S. C., and Chow, W. -S., *Int. J. Pharm.* 29, 161–168, 1986.
9. Suzuki, M., Ueka, S., and Kusai, A., *Chem. Pharm. Bull* 36, 720–725, 1988.
10. Szejtli, J., in *Cyclodextrin Technology*, Kluwer Academic Publ., Dordrecht, The Netherlands, 1988.
11. Torres-Labandeira, J., Davignon, P., and Pitha, J., *J. Pharm. Sci.*, accepted for publication, June '90.
12. Vikmon, M., Stadler-Szoke, A., and Szejtli, J., *J. Antibiot* 38, 1822–1824, 1985.

What is claimed is:

1. An amorphous hydroxypropylcyclodextrin:lipophile complex prepared by a process comprising the steps of dissolving a hydroxypropylcyclodextrin and a lipophile in an aqueous solution comprising a volatile co-solvent, and evaporating or lyophilizing the solution to dryness, to give the amorphous complex.

2. The amorphous complex recited in claim 1, wherein the hydroxypropylcyclodextrin is hydroxypropyl-$\beta$-cyclodextrin.

3. The amorphous complex recited in claim 1, wherein hydroxypropylcyclodextrin is hydroxypropyl-$\alpha$-cyclodextrin.

4. The amorphous complex recited in claim 1, wherein hydroxypropylcyclodextrin is hydroxypropyl-$\gamma$-cyclodextrin.

5. The amorphous complex recited in claim 1, wherein the volatile co-solvent is aqueous ethanol in concentrations of 70–95%.

6. The amorphous complex recited in claim 1, wherein the lipophile is a steroid.

7. The amorphous complex recited in claim 6, wherein the steroid is 5-androstene-3$\beta$,17$\beta$-diol, 4-androstene-3,17-dione, dehydroepiandrosterone, dexamethasone, 5-$\alpha$-dihydrotestosterone, 6-methylprednisolone, or testosterone.

8. The amorphous complex recited in claim 1, wherein the lipophile is a lipophilic peptide.

9. The amorphous complex as recited in claim 8, wherein the lipophilic peptide is gramicidin S.

10. The amorphous complex as recited in claim 1, wherein the volatile co-solvent is ammonia in concentrations of 2–20%.

11. The amorphous complex as recited in claim 10, wherein the lipophile is a macrocyclic antibiotic.

12. The amorphous complex as recited in claim 11, wherein the macrocyclic antibiotic is amphotericin B.

13. The amorphous complex as recited in claim 1, wherein the lipophile is vitamin D.

14. The amorphous complex as recited in claim 1, wherein the lipophile is vitamin E.

15. A pharmaceutical composition comprising:
an effective amount of an amorphous hydroxypropylcyclodextrin:lipophile inclusion complex prepared by a process comprising the steps of dissolving a hydroxypropylcyclodextrin and a lipophile in an aqueous solution comprising a volatile cosolvent, and evaporating or lyophilizing the solution to dryness, to give the amorphous complex; and a pharmaceutically acceptable carrier thereof.

16. A pharmaceutical composition as recited in claim 15, wherein the lipophile is a steroid.

17. A pharmaceutical composition as recited in claim 15, wherein the lipophile is a lipophilic peptide.

18. A pharmaceutical composition as recited in claim 15, wherein the lipophile is a lipophilic vitamin.

19. A pharmaceutical composition as recited in claim 18, wherein said vitamin is vitamin D or vitamin E.

* * * * *